United States Patent [19]

Gersh et al.

[11] Patent Number: 4,627,284
[45] Date of Patent: Dec. 9, 1986

[54] ULTRAVIOLET ABSORPTION HYGROMETER

[75] Inventors: Michael E. Gersh, Bedford; Fritz Bien, Concord; Lawrence S. Bernstein, Bedford, all of Mass.

[73] Assignee: Spectral Sciences, Inc., Burlington, Mass.

[21] Appl. No.: 757,165

[22] Filed: Jul. 22, 1985

[51] Int. Cl.[4] .............................................. G01W 1/00
[52] U.S. Cl. ................................. 73/336.5; 250/504 R
[58] Field of Search ............................. 73/335, 336.5; 250/504 R, 372

[56] References Cited

U.S. PATENT DOCUMENTS

| | | | |
|---|---|---|---|
| 2,979,950 | 4/1961 | Leone | 73/336.5 |
| 3,037,387 | 6/1962 | Friedman et al. | 73/336.5 |
| 3,636,768 | 1/1972 | Tinet et al. | 73/336.5 |
| 3,935,922 | 2/1976 | Cooper et al. | 250/461.1 |
| 4,066,904 | 1/1978 | Bertaux et al. | 250/372 |
| 4,403,826 | 9/1983 | Presby | 250/372 |
| 4,493,114 | 1/1985 | Geller et al. | 250/372 |
| 4,526,034 | 7/1985 | Campbell et al. | 73/336.5 |

FOREIGN PATENT DOCUMENTS 819649  4/1981  U.S.S.R. .............................. 73/336.5

OTHER PUBLICATIONS

Tilman; Water Vapor Density Measurements Utilizing the Absorption of Vacuum Ultraviolet and Infrared Radiation.

*Primary Examiner*—Stewart J. Levy
*Assistant Examiner*—Hezron E. Williams
*Attorney, Agent, or Firm*—Joseph S. Iandiorio; William E. Noonan

[57] ABSTRACT

An ultraviolet absorption hygrometer is provided including a source of pulsed ultraviolet radiation for providing radiation in a first wavelength region where water absorbs significantly and in a second proximate wavelength region where water absorbs weakly. Ultraviolet radiation in the first and second regions which has been transmitted through a sample path of atmosphere is detected. The intensity of the radiation transmitted in each of the first and second regions is compared and from this comparison the amount of water in the sample path is determined.

31 Claims, 5 Drawing Figures

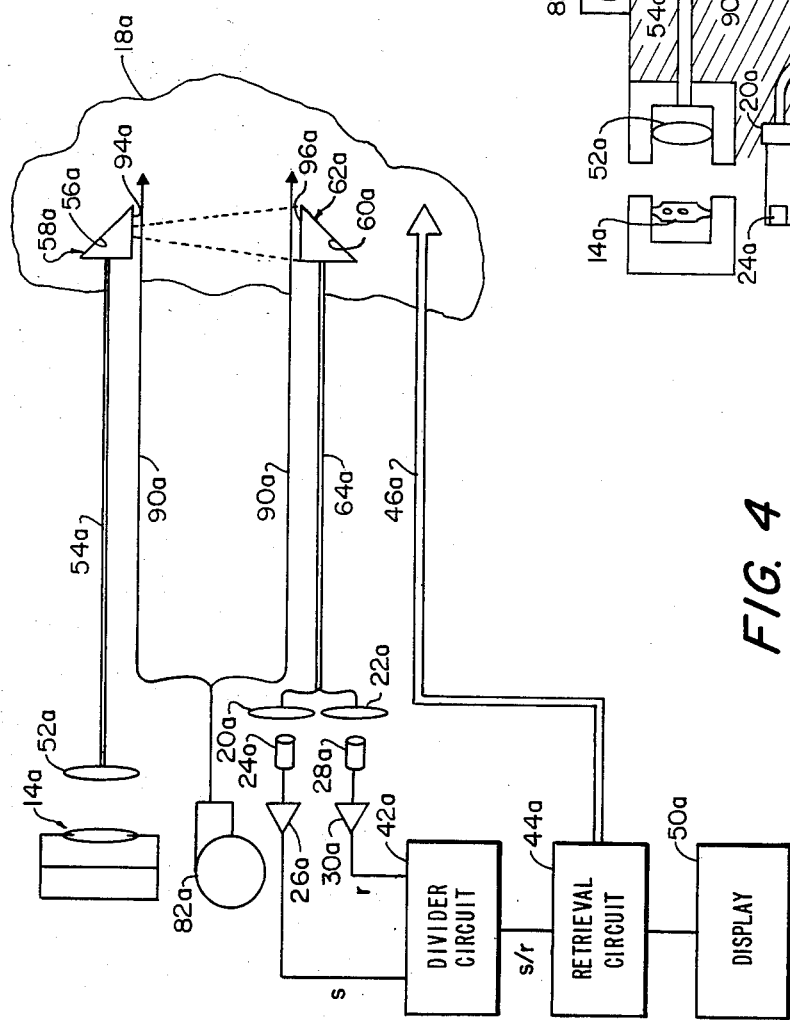
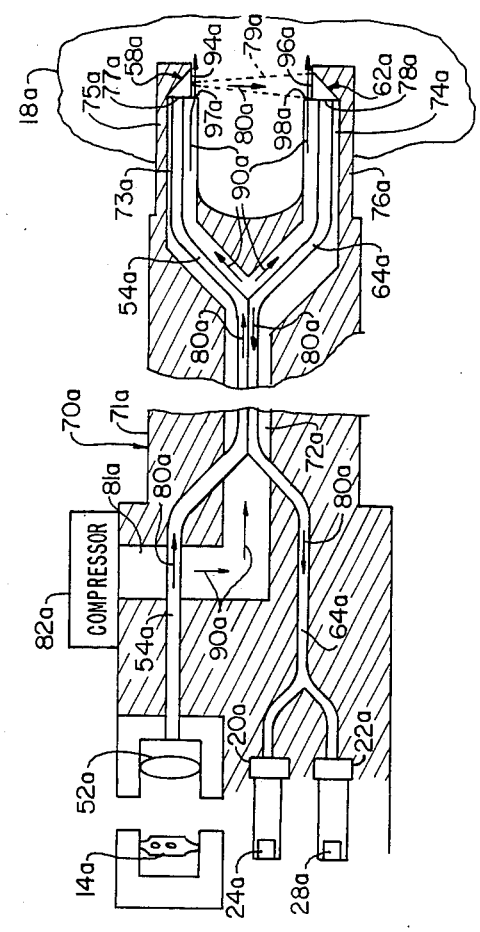
FIG. 4
FIG. 5

ULTRAVIOLET ABSORPTION HYGROMETER

This invention was made with government support under contract number DE-AC02-84ER80142 awarded by the Department of Energy. The government has certain rights in this invention.

FIELD OF INVENTION

This invention relates to an ultraviolet absorption hygrometer and more particularly to a hygrometer which employs pulsed ultraviolet radiation transmitted through a sample gas and measured in a pair of spectral bandwidths.

BACKGROUND OF INVENTION

Conventional humidity measurement is typically done optically using infrared detection systems. Such systems are large and employ continuous infrared radiation sources. Because of their relatively large thermal inertia, such infrared sources cannot be effectively pulsed and instead mechanical choppers must be used to provide the modulated signals required by the devices. Additionally, conventional infrared detectors are sensitive to background heat which includes infrared radiation.

Ultraviolet humidity detectors have been provided which employ a Lyman-Alpha hydrogen source. One such device dissociates water into its constituent OH radicals and hydrogen atoms. The emission spectra of the OH radicals are measured to indicate the amount of water present in the atmosphere. Another such device monitors the reduced transmission of the Lyman-Alpha source emission directly to determine humidity. These systems use continuous UV sources which are not extremely reliable and have a limited life. Therefore they are generally not viable for commercial use and have been employed primarily for research.

There is an ultraviolet oxygen ($O_2$) detector which employs two very close emission isotope lines from a continuous source. One of these lines is absorbed by $O_2$; the other is not. However, the water absorption at each of these wavelengths is virtually the same and therefore the system is impractical for measuring humidity.

SUMMARY OF INVENTION

It is therefore an object of this invention to provide an improved hygrometer which is rugged and yet small, lightweight and compact.

It is a further object of this invention to provide an ultraviolet hygrometer which exhibits low power requirements.

It is a further object of this invention to provide an ultraviolet hygrometer which does not require mechanical choppers or other moving parts.

It is a further object of this invention to provide an ultraviolet hygrometer which operates effectively in high temperatures and in sunlight.

It is a further object of this invention to provide an ultraviolet hygrometer which operates effectively without fouling in dirty and corrosive environments.

It is a further object of this invention to provide an ultraviolet hygrometer which exhibits effective temperature compensation and which effectively monitors high relative humidity.

It is a further object of this invention to provide an ultraviolet hygrometer which remains calibrated over relatively long periods of time.

It is a further object of this invention to provide an ultraviolet hygrometer which may be employed in a wide variety of meteorological, environmental and industrial applications.

This invention features an ultraviolet absorption hygrometer which includes a source of pulsed ultraviolet radiation for providing radiation in the first wavelength region where water absorbs significantly and in a second proximate wavelength region where water absorbs weakly. There are means for detecting ultraviolet radiation in the first and second regions transmitted through a sample path of atmosphere. Means responsive to the means for detecting are provided for comparing the intensity of the radiation transmitted in each of the first and second regions and there are means responsive to the means for comparing for determining the amount of water in the sample path.

In a preferred embodiment, the first and second wavelength regions are between 1700 and 2100 Angstroms. A strobe circuit may be provided for periodically energizing and de-energizing the source to provide the pulsed ultraviolet radiation. The means for detecting may include a first filter for transmitting only radiation in the first wavelength region and a second filter for transmitting only radiation in the second wavelength region. A first photodetector may be provided for receiving the radiation transmitted by the first filter and a second photodetector may be employed for receiving radiation transmitted by the second filter. Alternatively, a first photosensor may sense only radiation in the first wavelength region and a second photosensor may sense only radiation in the second wavelength region. The means for comparing may include means for normalizing the intensity of the radiation transmitted in each of the first and second regions. For example, the means for comparing and the means for normalizing may include means for dividing the intensity of the radiation transmitted in the first region by the intensity of the radiation transmitted in the second region. Alternatively, the means for comparing and the means for normalizing may include means for subtracting the intensity of the radiation transmitted in the second region from the intensity of the radiation transmitted in the first region. Feedback means may be provided for controlling the intensity of the radiation transmitted in the second region.

The means for determining may include means for retrieving a stored predetermined value for the amount of water in the sample path corresponding to the compared intensities of the radiation transmitted in the first and second regions. In alternative embodiments the means for determining may include means for calculating the amount of water in the sample. Preferably, means are also provided for sensing the temperature of the sample. In such embodiments the means for determining are further responsive to the means for sensing for determining the amount of water in the sample path at the sensed temperature. The means for determining may include means for resolving the absolute humidity and/or the relative humidity in the sample path. Means may also be provided for displaying and/or recording the water content determined in the sample path.

Typically, conduit means are provided for conducting the radiation from the ultraviolet source to the means for detecting. Such conduit means may include first and second conduit portions separated by the sample path. A first optical means may be provided for receiving radiation from the first conduit portion and transmitting that radiation through the sample path and a second optical means may receive the radiation transmitted through the sample path and transmit that radiation to the second conduit portion. The conduit means may include fiber optics and the optical means may include prisms and reflective elements. A housing may be provided for holding the conduit portions with their ends fixed relative to the sample path. Means may also be employed for providing a fluid flow over the optical means to keep them clean of contaminants.

DESCRIPTION OF PREFERRED EMBODIMENT

Other objects, features and advantages will occur from the following description of a preferred embodiment and the accompanying drawings, in which:

FIG. 4 is a schematic diagram of an ultraviolet absorption hygrometer according to this invention having fiber optics for conducting ultraviolet radiation to and from a gaseous sample; and FIG. 5 is an elevational partly cross-sectional, partly schematic view of one implementation of the ultraviolet absorption hygrometer of FIG. 4.

Figure 1:
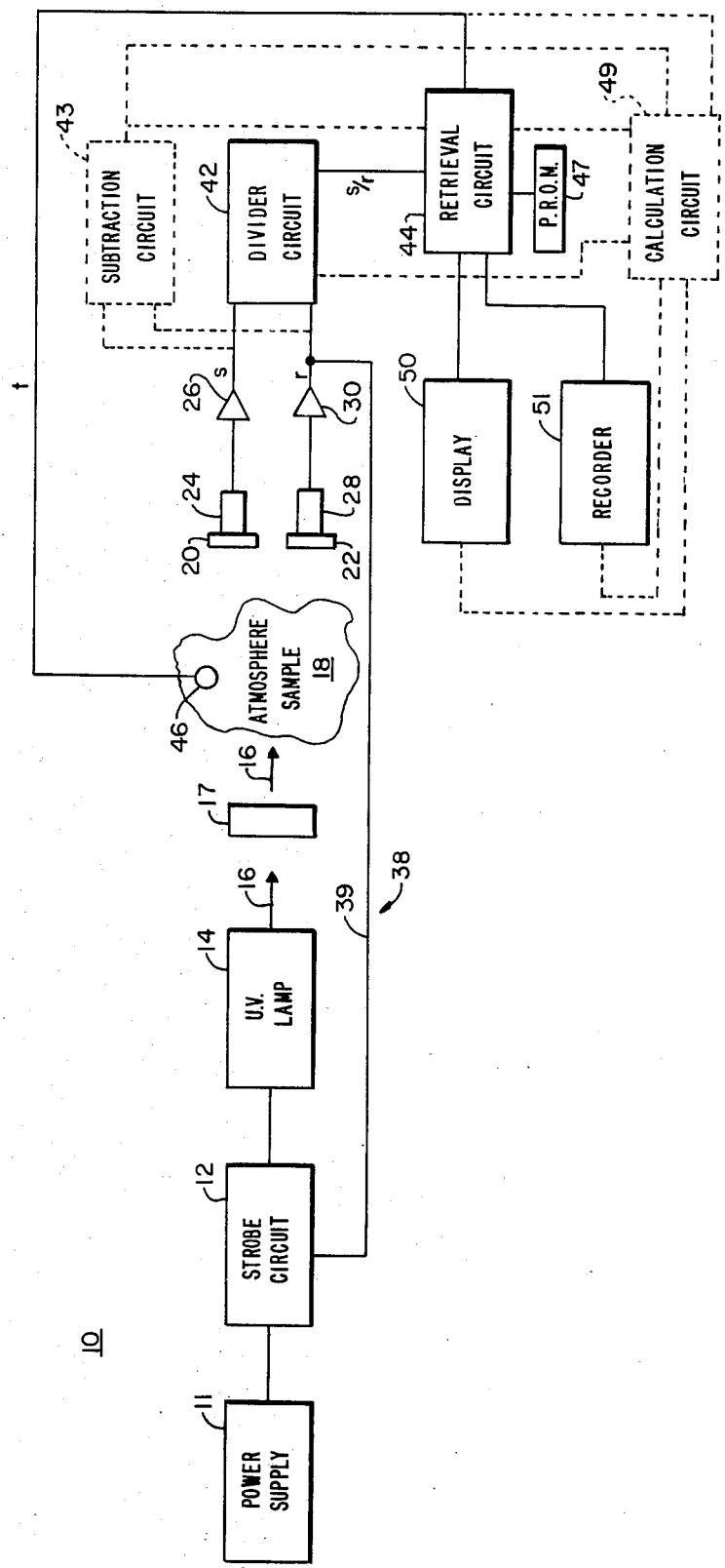
FIG. 1 is a schematic diagram of an ultraviolet absorption hygrometer according to this invention.

An ultraviolet absorption hygrometer according to this invention may be accomplished using a source of ultraviolet radiation for providing radiation in a first wavelength region where water absorbs significantly and in a second proximate wavelength region where water absorbs weakly. The source typically features an ultraviolet lamp which includes a rare gas such as Xenon enclosed within a water-free ultraviolet transmitting quartz envelope. Various alternative ultraviolet transmitting envelopes and lamp gases may be employed. Means such as a strobe circuit is provided for pulsing the radiation source to provide pulses typically on the order of 10 to 100 millijoules (although higher and lower energy pulses may be employed) and at a rate of approximately one pulse per second. Pulsing the source reduces the power requirements of the device considerably.

The first and second wavelength regions are preferably located between 1700 and 2100 Angstroms in the ultraviolet radiation range, and each of the regions is typically between 50 and 100 Angstroms bandwidth. These bandwidths are only representative, however, and this invention is not limited to them. The wavelength regions are selected depending upon the humidity levels to be encountered. For example, where the samples to be tested have relatively high water content, relatively long wavelengths are absorbed. However, in less humid samples, shorter wavelengths are absorbed. By determining which wavelengths exhibit the best absorption for a given humidity the operator is able to select the wavelength regions to be used and calibrate the hygrometer accordingly. The region of significant absorption by water typically occurs between 1700 and 1900 Angstroms, with significant absorption at 1850 Angstroms indicating a relatively humid sample. The region of relatively weak absorption by water is typically selected from the bandwidth between 1900 and 2100 Angstroms.

Means are provided for detecting ultraviolet radiation in the first and second regions which has been transmitted through a sample path of atmosphere. Typically a pair of filters such as solar blind ultraviolet bandpass filters available through Acton Research, Inc. transmit only radiation in the first and second wavelength ranges, respectively, and such radiation is detected by a pair of photodiodes such as provided by Hamamatsu, Inc. or other photodetectors. Because solar blind filters are employed, thermal and other background radiation does not affect measurements taken by the device. Alternatively, photosensors which are themselves sensitive only to the respective wavelength regions may be employed. For example, a cesium iodide (CsI) detector with a suprasil window is particularly effective for sensing light in only the first wavelength region.

A pair of signals, representative of the intensity of the radiation detected in the first and second regions are compared and may be normalized by dividing, subtracting or otherwise. Normalization of the signals from the first and second regions permits the hygrometer to be operated over extended periods without the need for constant recalibration. The signal representing the intensity of radiation in the second region may be provided to the strobe circuit through a silicon controlled rectifier (SCR) feedback loop to control the UV pulse duration and the intensity of the ultraviolet radiation. For example, when the appropriate photodiode senses that the intensity of the radiation in the second region has reached a predetermined reference level, the feedback means automatically shuts off the lamp.

Means responsive to the means for comparing are provided for determining the amount of water in the sample path. For example, a microprocesser or other means may be provided for calculating the water content. Alternatively, a retrieval circuit may be programmed to retrieve, from calibration data or curves or otherwise, a stored predetermined value for the amount of water in the sample path corresponding to the compared intensities of the radiation transmitted in the first and second regions. The means for determining is also typically responsive to a temperature sensor such as a thermocouple for determining the amount of water in the sample path at a particular sensed temperature. The means for determining may employ signals from the temperature sensor and the means for comparing in processing electronics to resolve absolute humidity and relative humidity.

An LED, LCD, analog device or other means may be provided for displaying the water content in the sample path and a computer printout, recorder or other acceptable means may be provided for recording the determined water content.

In one preferred embodiment the hygrometer of this invention employs conduit means such as fiber optics for transmitting the radiation from the UV source to the detectors. For example, the device may include first and second fiber optic portions separated by the sample path. First optical means such as a prism having a silvered surface or another type of reflective element is disposed proximate the end of the first fiber optic portion for receiving the radiation and transmitting that radiation through the sample path. A similar second optical means is provided for receiving the radiation which has been transmitted through the sample path and directing that radiation to the second fiber optic portion. A flow of air or other fluid from a compressor or other acceptable means may be provided over the optical means to keep them free of contaminants. The fluid flow also assists in cooling the device. The fiber optics and optical means may be accommodated within a rugged housing which typically holds the optical fibers with their ends fixed relative to the sample path. These parts constitute a probe which may be conveniently inserted into high temperature, corrosive, and contaminated atmospheres (such as are contained in kilns and elsewhere), which cannot be directly entered by the operator.

The above embodiment includes no moving parts and is able to operate under a wide range of mechanical and thermal stresses and in all ranges of relative humidity. The hygrometer of this invention is effective for use in a wide variety of meteorological and industrial applications such as high purity material and chemical manufacturing processes employed in the semiconductor industry, and elsewhere and the industrial drying of lumber, grain and other materials.

There is shown in FIG. 1 an ultraviolet absorption hygrometer 10 including a power supply 11 which activates a strobe circuit 12. The strobe operates an ultraviolet light source 14, to emit at approximately one-second intervals ultraviolet light pulses 16 which pass through a diffuser/baffle 17 and then a sample 18. A first filter 20 transmits only radiation in a first wavelength region fifty to one hundred Angstroms wide (e.g., 1750–1850 Angstroms), which is significantly absorbed by water in sample 18. A second filter 22 transmits only radiation in a second wavelength region approximately fifty to one hundred Angstroms wide (e.g. 1900–2000 Angstroms) which is proximate the first wavelength region but which is absorbed by water only weakly. Radiation in the first wavelength region is detected by a photodiode 24. Amplifier 26, connected to photodiode 24 provides a signal s, indicative of the intensity of the absorbed wavelength bandwidth transmitted through sample 18. Radiation in the second region is detected by a photodiode 28. A second amplifier 30 connected to photodiode 28 provides a reference signal r indicative of the intensity of the weakly absorbed wavelength region transmitted through sample 18.

The intensity of radiation pulses 16 is controlled by a feedback system 38. Amplified reference signal r is fed back through line 39 of system 38 to strobe circuit 12 to control the duration of pulses 16 so that the intensity of those pulses is set at a predetermined level, e.g., so that the reference signal does not exceed r. Line 39 provides pulses 16 having a uniform intensity and normalizes signals r and s to eliminate spurious signals caused by contaminants in sample 18.

Signals s and r are divided in divider circuit 42 to provide the signal s/r. In alternative embodiments the reference signal r may be subtracted from the signal s in subtraction circuit 43. Either of these circuits normalizes signals r and s where normalization has not been accomplished by a feedback circuit. Signal s/r is employed in retrieval circuit 44 to determine the water content of sample 18. Temperature sensor 46 monitors the ambient temperature of sample 18 and provides a signal t indicative of that temperature to circuit 44. Absolute humidity and/or relative humidity may be retrieved in circuit 44 from calibration curves entered in a programmable read-only memory 47. More typically absolute humidity alone is retrieved in circuit 44 and that value and temperature signal t are provided to a calculation circuit 49 where relative humidity is calculated using a conventional algorithm described more fully in connection with FIG. 3.

Alternatively, water content may be determined by entering both signal s/r from divider circuit 42 and the temperature signal t directly into a calculation circuit 49. The determined absolute and/or relative humidities are shown on display 50 and may be recorded on recorder 51.

Figure 2:
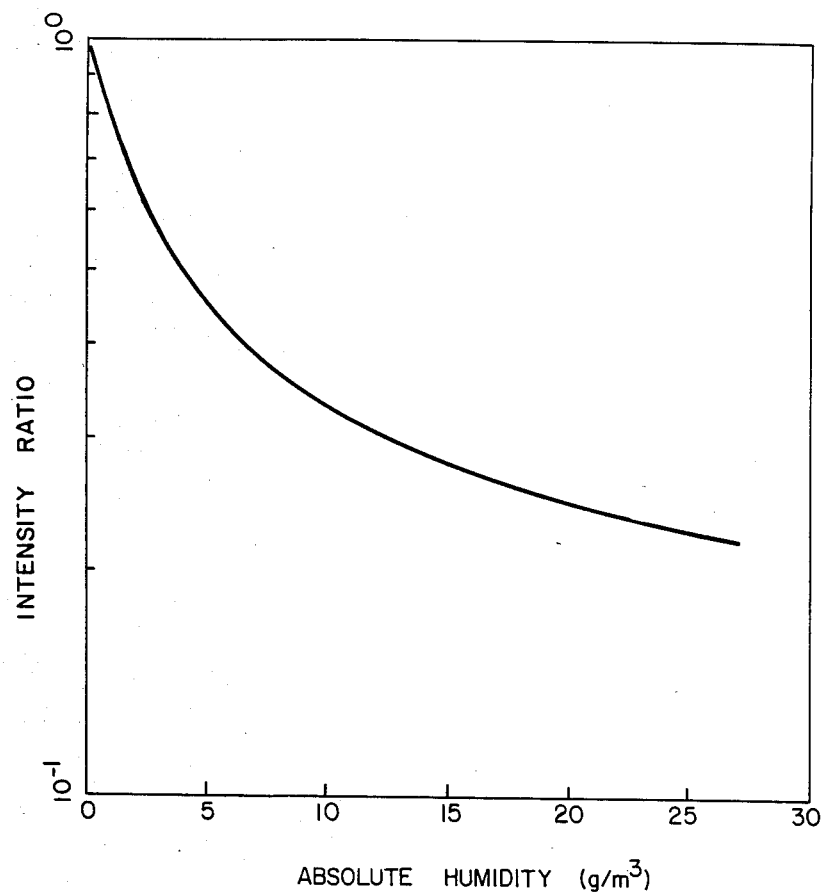
FIG. 2 is a curve illustrating calibrated values of absolute humidity versus intensity ratio signal for a particular temperature.

A representative calibration curve which may be used by circuit 44 for retrieving predetermined absolute humidity values is shown in FIG. 2. Values along the y axis represent the signal ratio s/r and values along the x axis indicate absolute humidity. The curve represents the values of s/r and absolute humidity for a sample at room temperature. This curve is compiled by employing samples having known absolute humidities and a predetermined temperature (e.g., room temperature) and measuring the values s/r for such samples. Slightly different curves are provided for different temperature samples.

Figure 3:
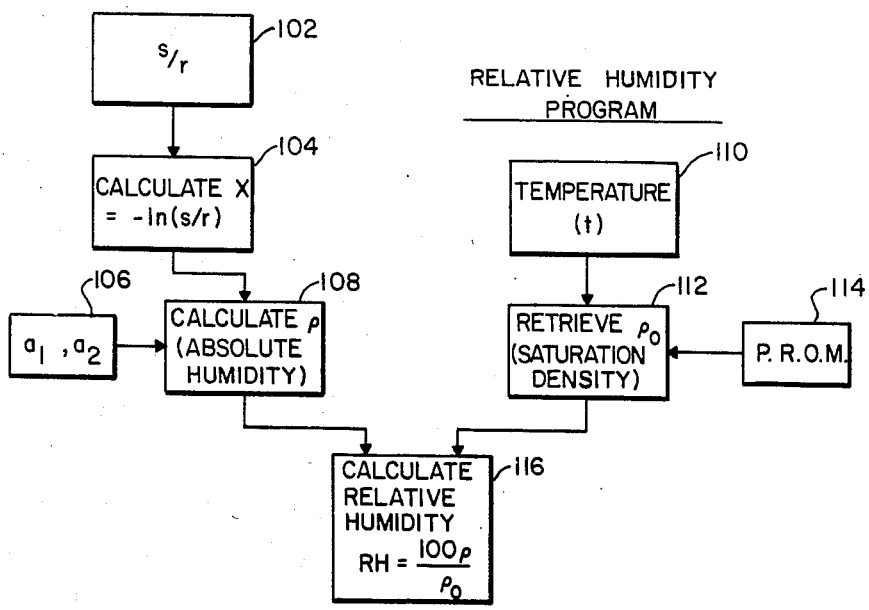
FIG. 3 is a block diagram of means for calculating absolute and relative humidity.

Representative software for calculating absolute and relative humidity in circuit 49 is shown in FIG. 3. To resolve the absolute humidity signal s/r is first obtained, step 102. The value $x = -\ln(s/r)$ is then calculated, step 104. The value x is equivalent to $a_1\rho + a_2\rho^2 + \ldots a_n\rho^n$ where $\rho$ is the atmospheric water vapor density (absolute humidity) and $a_1, a_2 \ldots a_n$ are coefficients which are determined by calibrating the system using n samples having known absolute humidities ($\rho$): The s/r signal is measured, and therefore the value x, is determined. Solving for $a = x/\rho$ for each sample yields the coefficient a for that sample. As the order of $\rho$ and the number of coefficients (i.e., the number n) is increased, so is the accuracy of x.

In the program shown in FIG. 3 a pair of coefficients $a_1, a_2$, determined in the above manner, are provided, step 106 and $x = a_1\rho + a_2\rho^2$. Absolute humidity is obtained by calculating $$\rho = \frac{-(a_1/a_2) \pm \sqrt{(a_1/a_2)^2 + 4x}}{2}$$

in step 108.

To solve for relative humidity temperature t is obtained, step 110. The saturation density $\rho_o$ is then retrieved, step 112, from values stored in a read-only memory 114. In alternative embodiments the saturation density $\rho_o$ may be obtained by calculating $\rho_o$ using a conventional parametric equation that represents the dependence of $\rho_o$ on t. The relative humidity RH is provided by solving for $RH = 100\rho/\rho_o$, step 116.

The absorption hygrometer of this invention may be employed as shown in FIG. 4 to monitor the water content of samples in high temperature dirty environments such as kilns. UV lamp 14a directs pulsed radiation through a lens 52a and an optical fiber 54a. The radiation is reflected from silvered surface 56a of a prism 58a to pass through the monitored sample 18a. The ultraviolet light is then reflected from a silvered surface 60a of a second prism 62a and directed through a return fiber 64a to filters 20a and 22a. Filter 20a transmits only light in a wavelength region which is significantly absorbed by the water in sample 18a. Filter 22a transmits only light in a wavelength band which is not absorbed by water in the sample. The radiation which is significantly absorbed by the water is detected by photodetector 24a. The radiation which is not absorbed by the water is detected by photodetector 28a. Amplifiers 26a and 30a provide respective amplified signals s and r, which are divided in divider circuit 42a. A temperature monitor 46a provides a sample temperature signal which is delivered to retrieval circuit 44a along with signal s/r from divider circuit 42a. The water content of sample 18a is determined as previously described and displayed on display 50a.

As shown more fully in FIG. 5, hygrometer 10a is constructed as a probe 70a which is inserted into a kiln or other container with an atmospheric sample to be measured. Probe 70a includes a housing 71a made of aluminum or similar material and having an axial passageway 72a which branches into passageways 73a, 74a in arms 75a, 76a. Optical fiber 54a extends through passageways 72a and 73a between lens system 52a and prism 58a and fiber 64a returns through passageways 74a and 72a from prism 62a to filters 20a, 22a. Arms 75a, 76a of probe 70a are inserted into atmosphere sample 18a. Housing 71a fixes the ends 77a, 78a of fibers 54a and 64a and prisms 58a, 62a with respect to sample path 79a. As indicated by arrow 80a, UV radiation from source 14a travels through fiber 54a, across sample path 79a and back through fiber 64a for filtering and detection.

An opening 81a interconnects a compressor 82a with axial passageway 72a. Compressor 82a blows currents of clean air, as indicated by arrows 90a, through passageways 72a, 73a and 74a, out through exits 97a, 98a proximate the ends of respective arms 75a, 76a and across surfaces 94a, 96a of prisms 58a and 62a. This air flow keeps surfaces 94a and 96a free from contaminants which may otherwise foul the prisms and interfere with transmission of radiation through the optical fibers and with the accuracy of measurements taken by the system.

Although specific features of the invention are shown in some drawings and not others this is for convenience only as each feature may be combined with any or all of the other features in accordance with the invention.

Other embodiments will occur to those skilled in the art and are within the following claims:

What is claimed is:

1. An ultraviolet absorption hygrometer comprising: a source of pulsed ultraviolet radiation for providing in each pulse radiation both in a first wavelength region where water absorbs significantly, and in a second proximate wavelength region where water absorbs weakly; means for detecting ultraviolet radiation respectively in said first and second regions transmitted through a single sample path of gas; means, responsive to said means for detecting, for comparing the intensity of the radiation transmitted in each of the first and second regions; and means, responsive to said means for comparing, for determining the amount of water in the sample path.

2. The hygrometer of claim 1 in which said first and second wavelength regions are between 1700 and 2100 Angstroms.

3. The hygrometer of claim 1 further including a strobe circuit for periodically energizing and de-energizing said source to provide the pulsed ultraviolet radiation.

4. The hygrometer of claim 1 in which said means for detecting includes a first filter for transmitting only radiation in said first wavelength region and a second filter for transmitting only radiation in said second wavelength region.

5. The hygrometer of claim 4 further including a first photodetector for receiving radiation transmitted by said first filter and a second photodetector for receiving radiation transmitted by said second filter.

6. The hygrometer of claim 1 in which said means for comparing includes means for normalizing the intensity of the radiation transmitted in each of said first and second regions.

7. The hygrometer of claim 6 in which said means for comparing and said means for normalizing includes means for dividing the intensity of the radiation transmitted in said first region by the intensity of the radiation transmitted in said second region.

8. The hygrometer of claim 6 in which said means for comparing and said means for normalizing includes means for subtracting the intensity of the radiation transmitted in said second region from the intensity of the radiation transmitted in the first region.

9. The hygrometer of claim 1 in which said means for determining includes means for retrieving a stored predetermined value for the amount of water in the sample path corresponding to the compared intensities of the radiation transmitted in said first and second regions.

10. The hygrometer of claim 1 in which said means for determining includes means for calculating the amount of water in the sample.

11. The hygrometer of claim 1 further including means for sensing the temperature of said sample, said means for determining being further responsive to said means for sensing for converting the determined amount of water in the sample into water of relative humidity.

12. The hygrometer of claim 1 in which said means for determining includes means for resolving the absolute humidity in the sample path.

13. The hygrometer of claim 1 in which said means for determining includes means for resolving the relative humidity in the sample path.

14. The hygrometer of claim 1 further including feedback means for controlling the intensity of the radiation transmitted in said second region.

15. The hygrometer of claim 1 further including means responsive to said means for determining for displaying the water content determined in the sample path.

16. The hygrometer of claim 1 further including means responsive to said means for determining for recording the water content determined in the sample path.

17. The hygrometer of claim 1 further including conduit means for conducting said radiation from said source to said means for detecting.

18. The hygrometer of claim 17 in which said conduit means includes first and second conduit portions separated by said sample path.

19. The hygrometer of claim 18 including first optical means for receiving radiation from said first conduit portion and transmitting said radiation through the sample path and second optical means for receiving the radiation transmitted through the sample path and transmitting it to said second conduit portion.

20. The hygrometer of claim 17 in which said conduit means includes fiber optics.

21. The hygrometer of claim 18 further including a housing for holding said conduit means with their ends fixed relative to said sample path.

22. The hygrometer of claim 19 in which said optical means include prisms.

23. The hygrometer of claim 19 further including means for providing a fluid flow over said optical means to keep said optical means clean of contaminants.

24. The hygrometer of claim 19 in which said optical means include reflective elements.

25. The hygrometer of claim 1 in which said means for detecting includes a first photosensor which senses only radiation in said first wavelength region and a second photosensor which senses only radiation in said second wavelength region.

26. An ultraviolet hygrometer comprising:
a source of pulsed ultraviolet radiation for providing radiation in a first wavelength region where water absorbs significantly and in a second proximate wavelength region where water absorbs weakly;
a housing including conduit means for conducting said radiation therethrough, said conduit means having first and second portions separated by a space for containing a sample path;
means for detecting ultraviolet radiation in said first and second regions transmitted through the sample path;
means, responsive to said means for detecting, for comparing the intensity of the radiation transmitted in each of first and second regions; and
means, responsive to said means for comparing, for determining the amount of water in the sample path.

27. The hygrometer of claim 26 further including first optical means for receiving said radiation from said first conduit portion and transmitting said radiation through the sample path and second optical means for receiving the radiation transmitted through the sample path and transmitting said radiation to said second conduit portion.

28. The hygrometer of claim 27 in which said conduit means includes fiber optics.

29. The hygrometer of claim 27 in which said optical means include prisms.

30. The hygrometer of claim 27 in which said optical means include reflective elements.

31. The hygrometer of claim 26 further including means for providing a fluid flow over said optical means to keep said optical means clear of contaminants.

* * * * *